(12) United States Patent
Livelli et al.

(10) Patent No.: US 7,960,101 B2
(45) Date of Patent: *Jun. 14, 2011

(54) METHOD FOR USING DIVISION ARRESTED CELLS IN SCREENING ASSAYS

(75) Inventors: Thomas Livelli, Madison, WI (US); Zhong Zhong, Shanghai (CN); Mark Federici, Madison, WI (US); Mei Cong, Madison, WI (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/685,223

(22) Filed: Jan. 11, 2010

(65) Prior Publication Data

US 2010/0203561 A1 Aug. 12, 2010

Related U.S. Application Data

(60) Continuation of application No. 12/138,218, filed on Jun. 12, 2008, now abandoned, which is a continuation of application No. 11/363,983, filed on Feb. 27, 2006, now abandoned, which is a division of application No. 10/251,467, filed on Sep. 20, 2002, now Pat. No. 7,045,281.

(51) Int. Cl.
*C12Q 1/00* (2006.01)
*C12Q 1/68* (2006.01)
*G01N 33/53* (2006.01)
*C12P 1/00* (2006.01)

(52) U.S. Cl. .................. 435/4; 435/6; 435/7.95; 435/41

(58) Field of Classification Search .................. None
See application file for complete search history.

(56) References Cited

U.S. PATENT DOCUMENTS

| | | | |
|---|---|---|---|
| 5,998,136 | A | 12/1999 | Kamb |
| 6,875,576 | B2 | 4/2005 | Carreras |
| 6,897,067 | B2 | 5/2005 | Uhler |
| 7,045,281 | B2 * | 5/2006 | Livelli et al. ............ 435/4 |
| 2001/0046497 | A1 | 11/2001 | Zhang |
| 2008/0081327 | A1 | 4/2008 | Livelli et al. |
| 2008/0248516 | A1 | 10/2008 | Livelli et al. |

FOREIGN PATENT DOCUMENTS

| | | |
|---|---|---|
| WO | WO-02/42447 | 5/2002 |
| WO | WO-02064092 A2 | 8/2002 |
| WO | WO 2003/034803 | 5/2003 |

OTHER PUBLICATIONS

Barak, Larry S., et al., "Real-time Visualization of the Cellular Redistribution of G Protein-coupled Receptor Kinase 2 and β-Arrestin 2 during Homologous Desensitization of the Substance P Receptor", The Journal of Biological Chemistry, vol. 274, No. 11, pp. 7565-7569, Mar. 12, 1999.

Cho, G., et al., The transcriptional repression of the human Cu/Zn superoxide dismutase (sod1) gene by anticancer drug, mitomycin C(MMC), Biochem Mol Bio Int, 42(5):949-56, Aug. 1997.

Fueger, Barbara J., et al., "Effects of Chemotherapeutic Agents on Expression of Somatostatin Receptors in Pancreatic Tumor Cells", The Journal of Nuclear Medicine, vol. 42, No. 12, pp. 1856-1862, Dec. 2001.

Goetz, AS, et al., Development of a facile method for high throughput screening with reporter gene assays, J Biomol Screen, 5(5): 377-84, Oct. 2000.

Hudson, James D., "A Proinflammatory Cytokine Inhibits p53 Tumor Suppressor Activity," J. Exp. Med., vol. 190, No. 10, pp. 1375-1382, Nov. 15, 1999.

Kharbanda, Surender, et al., "Activation of the c-Abl tyrosine kinase in the stress response to DNA-damaging agents", Nature, vol. 376:31, 785-788, Aug. 1995.

King, K., et al., "Control of yeast mating signal transduction by a mammalian beta 2-adrenergic receptor and Gs alpha subunit", Science, 250 (4977), pp. 121-123; Oct. 5, 1990.

Müller, Martina, et al., "p53 Activates the CD95 (APO-1/Fas) Gene in Response to DNA Damage by Anticancer Drugs", J. Exp. Med., vol. 188, No. 11, pp. 2033-2045, Dec. 7, 1998.

Mundell, Stuart J., et al., "Selective Regulation of Endogenous G Protein-coupled Receptors by Arrestins in HEK293 Cells", The Journal of Biological Chemistry, vol. 275, No. 17, pp. 12900-12908, Apr. 2000.

Yao, Kang-Shen, et al., "Involvement of Activator Protein-1 and Nuclear Factor-κB Transcription Factors in the Control of the DT-Diaphorase Expression Inducted by Mitomycin C Treatment", Molecular Pharmacology, vol. 51, pp. 422-430, 1997.

EP03751966, "European Search Report Mailed Nov. 2, 2006", 3.

* cited by examiner

*Primary Examiner* — Prema Mertz

(57) ABSTRACT

Division arrested cells are used in screening assays to determine the effect of a substance of interest on the cells. The division arrested cells can be used in drug screening assays, signal transduction assays, and are especially useful in large scale, high throughput assays.

16 Claims, 3 Drawing Sheets

POP
Gr
10μM 5HT
50.0% positive

POP
Ar
10μM 5HT
61.9% positive

POP
Ar
10μM Mes.
10μM 5HT
0.1% positive

METHOD FOR USING DIVISION ARRESTED CELLS IN SCREENING ASSAYS

RELATED APPLICATIONS

This application is a continuation of U.S. patent application Ser. No. 12/138,218, filed Jun. 12, 2008, which is a continuation of U.S. patent application Ser. No. 11/363,983, filed Feb. 27, 2006, now abandoned, which is a divisional of U.S. patent application Ser. No. 10/251,467, filed Sep. 20, 2002, now U.S. Pat. No. 7,045,281, which applications are entirely incorporated herein by reference.

FIELD OF THE INVENTION

This invention relates to methods for screening for substances of interest. More particularly, it relates to screening assays which utilize cells in a division arrested state which, nonetheless, function effectively in assays where dividing cells would normally be used. The advantages of the system will be seen in the disclosure which follows.

BACKGROUND AND PRIOR ART

Cell based screening assays are tools well known to biologists. In the assays, one investigates compounds of interest to determine, e.g. if the compounds modulate one or more biological processes of interest.

Among the cell based systems which are used are those which measure reporter activity, calcium activity assay, and so forth. These, and all other cell based assays are encompassed by the invention.

One area where cell based screening assays have become widely accepted is the high throughput analysis of materials for use as pharmaceuticals. These assays are useful and desirable because compounds which are identified initially in biochemical assays have been known to fail as drug candidates later in the development process. The reasons for this are many. In some cases, the compound does not permeate the cell readily. In others, target binding capability is not predictive of the target modulating function, a feature that is, ultimately, a requirement of drug functions. Cell based screening assays are useful in that they address a number of problems associated with animal model testing (e.g., high expense, intensive labor, long assay period). High throughput cell based screening assays can be scaled up via technologies such as "FLIPR," "Leedseeker," "VIPR," and fluorescent, high speed cell-imaging.

In addition to assays such as those discussed supra, other commonly used, cell based assays involve enzyme-reporter systems, cell activity assays with a fluorescent or colorimetric readout, and so forth. An example of such an assay is a $Ca^{2+}$ mobilization assay to measure G-protein coupled receptor activity with the dye "Fluo-4."

In addition to the advantages set forth supra, cell based assays have a distinct advantage in that they permit the user to determine the functional outcome, of the use of compounds. Properly designed assays also permit the artisan to select against the toxic compounds, when screening for active ones.

Carrying out high throughput, cell based assays present unique challenges to users. Unlike pure biochemical reagent like enzymes, proteins, and membrane receptor preparations, cells are live dynamic entities. Preparation and cultivation have to be tied to the actual screening process.

Actively managed cell culture cycles have a recovery phase, when they are split from near confluent cultures, followed by an early log growth phase, then a mid log, and a late log phase, leading to a stationary phase if the culture is allowed to become confluent. Variances of the cellular processes and protein components at these different stages of growth and replication occur constantly during these cell cultures as cells cycle through mitosis. These variances must be expected to affect biological assays, and be a factor in the common phenomenon of variability in high throughput assays. One, but by no means the only example of this, relates to the length of time over which assays are run. There is generally an 8-36 hour period following the seeding of cells during which the assay is run. The cells in the particular culture go through different phases of their culture cycle during this time, and it is not usual for the cells to be at the same point in the cycle at the same time.

Further, the miniaturization of cell based screening assays is progressing, with smaller and smaller numbers of cells being used. As this occurs, sensitivity of the assay to variability increases rapidly and dramatically.

The critical factors of a good cell based screening assay are (i) a well validated target, (ii) a sensitive readout, and (iii) extremely high consistency of the cells that are used. The invention which is set forth in the disclosure which follows addresses this third issue. The consistent performance of the cells in an assay can be greatly affected by changes in the level of target expression as a result of increasing cell passage number. In addition, a well characterized population of cells can be division arrested, cryopreserved as a cell bank, and plated for an assay without any additional passaging of the cells. In fact, division arrested cells may be plated and used over a period of up to five (5) days without any further handling of the cells and without a significant change in cell based responses.

Division arrested cells have been used in the art. Exemplary of this are Cho, et al., *Biochem. Mol. Biol. Int.* 42:949 56 (1997); Yao, et al., *Mol. Pharmacol* 57:422 30 (1997); Fueger, et al., *J. Nucl. Med.* 42:1856 62 (2001); Muller, et al., *J. Exp. Med.* 188: 2033 45 (1998), and Kharbanda, et al., *Nature* 376 (6543):785-8 (1995). All of these references are incorporated by reference. Review of these, as well as other references will show that these studies concern characterization of the cells, rather than their use in assays of the type described herein, such as drug discovery, screening assays, and/or signal transduction assays, especially when these are carried out on a large scale, high throughput basis as is required for industrial application.

These, as well as other features of the invention will be elaborated upon in the disclosure which follows.

DETAILED DESCRIPTION OF PREFERRED EMBODIMENTS

Example 1

Figure 1A:
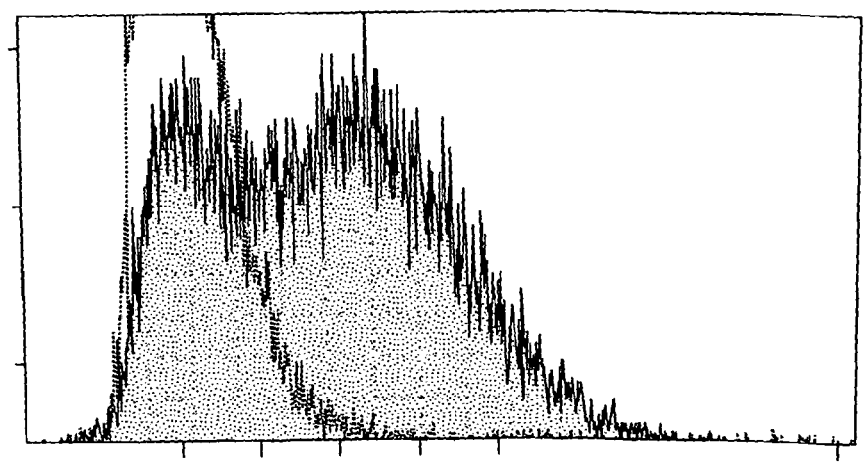
FIGS. 1A-1C set forth FACS scans depicting secrotonin induction of $Ca^{++}$ mobilization on division arrested cells, which are set forth in example 1.

These experiments describe screening assays designed to measure the induction of $Ca^{2+}$ mobilization by serotonin in growth arrested, NIH3T3 cells.

NIH3T3 cells were stably transfected with cDNA encoding the known receptor "5HT2c" using standard methods. For information on the receptor, see Julius, et al., Proc. Natl. Acad. Sci USA 87:928 32 (1990), incorporated by reference. After the transfection, and a preliminary screen to make sure that the transfection was successful, NIH3T3 cells which expressed the (4500 mg/L), together with 1× penicillin-streptomycin solution and 10% (v/v) fetal bovine serum (FBS). This cell line is referred to as "NIH3T3-POP."

In order to arrest the growth of the cells, they were exposed to 10 μg/ml of mitomycin C, for 2.5 hours. Mitomycin C is well known for its ability to arrest cell growth by blocking microtubule mobility, thereby arresting cell division. The cells were frozen, 2.5 hours after treatment, using standard protocols.

As a control, cells which were not exposed to mitomycin C were frozen using the same procedure. Samples of both treated and control cells were thawed, using standard methods, and plated for 24 hours, prior to harvest. Harvesting was accomplished by adding 7 ml of an enzyme free, cell dissociation solution, (e.g., EnzymeFree Cell Dissociation Solution, Specialty Media, catalog number S-014) or with 0.5 mM EDTA, to cells. The number of cells used in each experiment was $4 \times 10^5$ cells/ml or about 4 $4.5 \times 10^6$ total cells. Such solutions are widely available, and are well known to the skilled artisan. This treatment dissociated cells from the flask, and aggregates were then broken up by repeated pipetting of the suspensions, up and down in the flasks, so as to provide a good proportion of single cells, as this is necessary for the FACS analysis which followed.

Cells were pelleted, and then resuspended in 6 ml of Indo-1 loading buffer.

Cells were loaded with Indo-1 AM dye by adding 2 mg/ml of Indo-1 AM stock, in DMSO, to the cell suspensions to a final concentration of 10 μg/1.2 mls. Cells were exposed to Indo-1 AM for seven (7) minutes at room temperature and then diluted up to a final volume of 10 mls with Indo-1 loading buffer and pelleted.

In order to measure and to analyze $Ca^{2+}$ mobilization, a commercially available cell sorter was used. Excitation was set at 360 nm, and emissions were set at both 400 (±15 nm) and 500 (±20)nm. The emissions were monitored simultaneously, and the emission ratio at 400 nm/500 nm was used to report the intracellular rise of $Ca^{2+}$ concentration. Untreated cells were used to set a baseline ratio.

Cells were resuspended in a buffer and loaded into a syringe. Cells were injected continuously into the flow cytometer to be sampled and to provide a baseline value. A substance such as an antagonist can be used to pretreat the cells, with a second material, such as an agonist being injected continuously and simultaneously through, e.g., a second syringe, via a connecting means, such as a standard Y-connector. Cells are then exposed to the test substance, analyzed, and changes from baseline measured.

Figure 1B:
Figure 1C:

The data of the experiment are summarized in FIG. 1. Cells which had been division arrested (POP Ar 10 μM 5HT panel in FIG. 1) responded in a manner similar to those which were not (POP Gr 10 μM 5HT panel in FIG. 1). In brief, "% positive" was calculated by taking the percentage in the positive region (i.e., cells demonstrating an increase in intracellular $Ca^{++}$ concentration that is greater than the baseline $Ca^{++}$ concentration of unstimulated cells) The "% positive" value was used to measure the extent of activation induced by serotonin.

Actively growing NIH3T3 cells which expressed 5HT2c showed a 50% $Ca^{2+}$ response, while growth arrested cells showed a comparable 61.9% $Ca^{++}$ response. Control experiments indicated that the response was receptor specific. To elaborate, parental NIH3T3 cells which were not transfected showed no fluorescence change when treated with serotonin (data not shown), while pretreatment with antagonist (10 μM Mesulergine) blocked serotonin induction completely (POP Ar 10 μM 5HT, 10 μM Mes panel in FIG. 1). Only 0.1% of Mesulergine pretreated cells responded to serotonin in $Ca^{++}$ mobilization.

Example 2

These experiments were carried out to determine if the principles proven in example 1, supra, were applicable to other receptors, such as other Gq coupled receptors. To test this, cell line M1WT3 (ATCC CRL 1985) was chosen. This cell line expresses muscaranic acetylcholine receptor. Experiments were designed to determine if known agonists induce $Ca^{2+}$ mobilization in these cells after growth arrest.

M1WT3 cells were grown and treated, as set forth in example 1, supra. They were also treated with mitomycin C as described, and controls were prepared in exactly the same way.

Figure 2:
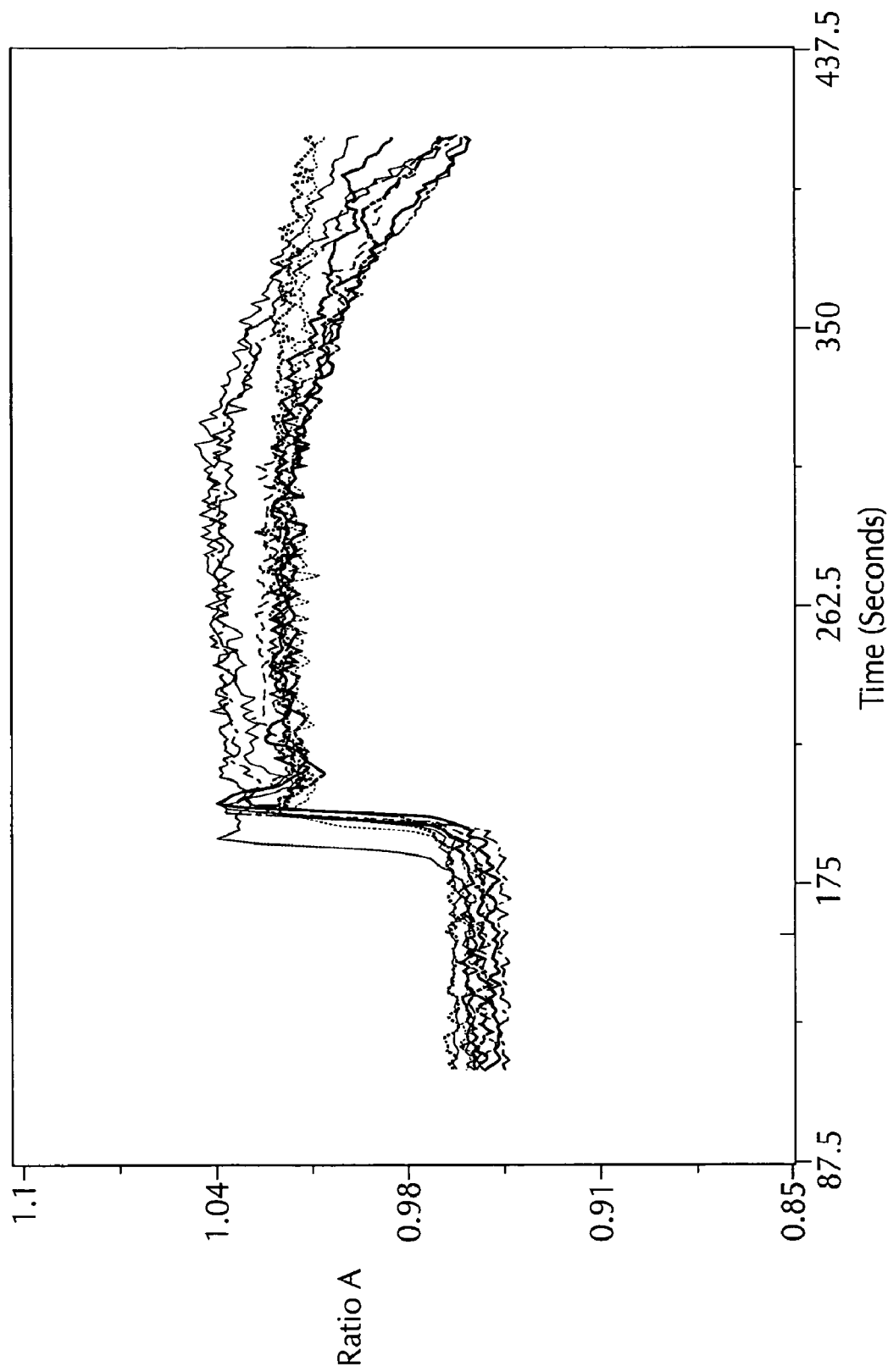
FIG. 2 shows the result of experiments, described in detail in example 2. It shows carbachol induced, $Ca^{2+}$ mobilization, observed via changes in fluorescent emission ratios of Fura2 loaded into cells that were induced.

A $Ca^{2+}$ imaging device was used to inspect $Ca^{2+}$ mobilization visually. To do this, cells were loaded with "Fura-2" a fluorescent, $Ca^{2+}$ indicator. Cells were excited at 340 and 380 nm wavelengths, and emission ratios were monitored at 450 nm. Carbachol induced, $Ca^{2+}$ mobilization was observed, in M1WT3 cells, via changes in fluorescent emission ratios, rising from approximately 0.94 to 1.03 in individual cells (FIG. 2). Mitomycin C pretreatment had no negative effect on the carbachol induced $Ca^{2+}$ response of the cells, when compared to cells not division-arrested (data not shown). It was shown that a larger percentage of division arrested cells responded to carbachol (data not shown), which is consistent with a more uniform cell population, resulting from the arrested division.

The results reported supra suggested that division arrested cells may be more consistent, over time, in screening assays. This was tested via a time-course cell imaging experiment. Division arrested and frozen cells were imaged as stimulated by serotonin 1, 3, 5 and 7 days following thawing of cells. Comparable percentage, and extent of $Ca^{2+}$ response were found, as measured by a Fura 2 fluorescence 340/380 ratio change, on these different days, while significant changes in $Ca^{2+}$ levels were found in growing populations on these different days.

Example 3

It is well known that G-protein coupled receptors elicit different pathways, depending on the G protein to which they couple. The experiments which follow were designed to show that seven-transmembrane receptors other than Gq coupled receptors function normally in growth arrested cells.

To do this, HEK293 cells which had been transfected stably and overexpressed the β2 adrenergic receptor ("β2AR") (which is a Gs coupled, seven-transmembrane receptor) was used, in experiments designed to determine if isoproterenol would induce CRE-SEAP reporter activity.

The stably transfected cells were grown in DMEM with 10% FBS, and then were transiently transfected with a reporter plasmid, i.e., pCRE-SEAP. The cells were treated with, mitomycin for 2 hours, 24 hours past transfection. The plasmid contained a CRE promoter, activity of which is elevated by cAMP, and which expresses higher levels of secreted, alkaline phosphatase ("SEAP") upon activation of GPCRs, which use cAMP as a second messenger.

Twenty-four hours after mitomycin C treatment, β2ARs were activated with 100 μM of isoproterenol, and the level of SEAP activity was measured using commercially available products, 24 hours later.

Actively growing β2 adrenergic receptor expressing cells responded to overnight treatment with 100 μM of isoproterenol, as measured by increased SEAP activity (approximately 25%). Growth arrested, β2AR expressing cells displayed much lower background SEAP activity, which may be attributable to mitomycin C toxicity. Notwithstanding the lower background levels, overnight stimulation with isproterenol induced a 2.5 fold increase in SEAP activity, thus demonstrating that growth arrested cells still conduct largely intact signal transduction pathways down to the transcription response, and enzyme reporter assays can be carried out in division arrested cells.

Miyotmycin C treatment caused significant toxicity to the β2AR expressing cells. As such, a different method for arresting cell division was tested, i.e., gamma irradiation.

Cells were either non-irradiated, and served as a control, or were irradiated at does ranging from 2Gy(Gray) to 8Gy. They were then treated with 100 μM isoproterenol, as described, supra. Reporter SEAP activity was measured, and compared to baseline activity (i.e., cells not treated with isoproterenol).

Figure 3:
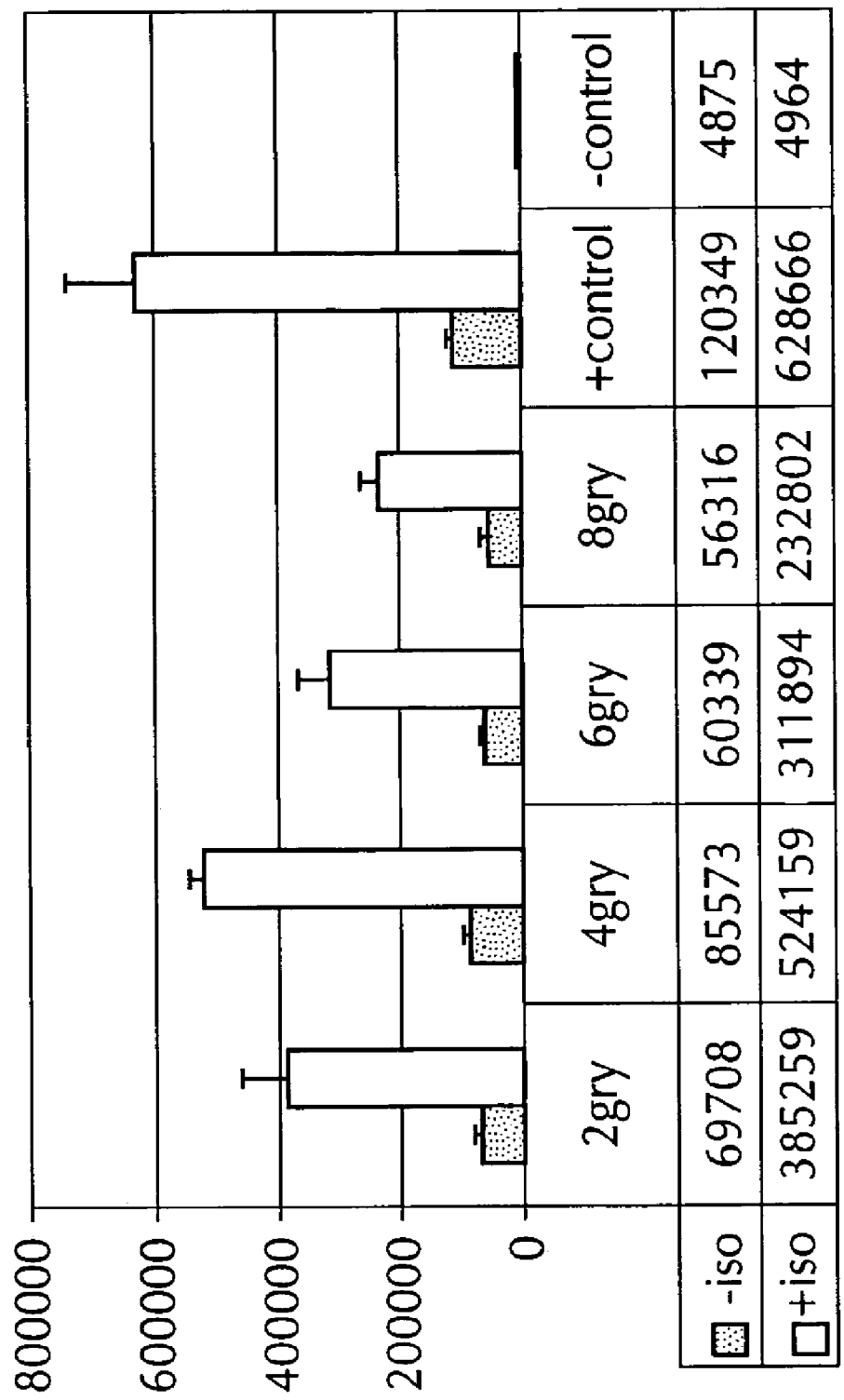
FIG. 3 summarizes the result of experiments set forth in example 3, involving cells where division was arrested by irradiation, and which were treated with isoproterenol and reporter gene changes were measured.

The results are depicted in FIG. 3. Cells which were treated with 4Gy or more gamma irradiation showed far greater division arrest, with no noticeable cell proliferation for about a week. These cells show normal cell morphology and, when stimulated with isoproterenol, SEAP responses ranged from 4 to 6 fold over the baseline levels. These results were comparable to the cells that had not been division arrested, which responded 5.2 fold over baseline upon stimulation with isoproterenol.

The foregoing discussion sets forth features of the invention, which relates, inter alia, to a method for screening for a substance of interest. The method comprises contacting the substance of interest with a sample of division arrested cells, and determining interaction between the division arrested cells and the substance of interest to determine one or more properties thereof. In this way, one can determine whether a substance of interest has efficacy as an antagonist, an agonist, an inhibitor, a stimulator, or a modulator of cells, is toxic to the cells, and so forth.

By division arrested as used herein is meant that the cells being used have been treated, by means known in the art, so that either their mitotic or meiotic cycle has been stopped, and cellular division can no longer take place. There are many chemical, radiological, and other methods which can be used to accomplish the arrest of cellular division, and these need not be reiterated here, as the crux of the invention is not the act of causing the arrest of cell division, but the use of the arrested cells in assays as described.

While it is possible to treat the cells in additional ways to arrest one or more additional biological processes, this is not necessary and, indeed, in many applications it will be desirable to have the cells function normally in all other ways but for the arrest in cell division.

It will be seen by the skilled artisan that the type of cell used may vary. Any prokaryotic or eukaryotic cell may be used, in any cell based assay to determine the effect of a substance of interest on a cell type of interest.

The nature of the cell type used will depend upon the particular type of assay to be run. To this end, cells which express a particular molecule or molecules naturally, or cells transfected or transformed to express the molecule or molecules of interest may be used. Prokaryotic cells, such as *E. coli*, which may be transformed with nucleic acid molecules, such as those which encode a eukaryotic receptor, and eukaryotic cells such as NIH3T3 cells, HEK293 cells, CHO cells, and so forth, can all be used. Other types of nucleic acid molecules may be used, including DNA encoding any protein of interest, RNA and antisense molecules, including antisense DNA and antisense RNA. Many methods are known for introducing the nucleic acid molecules to the host cells, such as via the use of recombinant viral vectors or other vectors that are adapted for the cell type of interest. Further, the cells may be cells which have been transduced with a molecule of interest, such as a peptide, and/or a protein containing a molecule such as a protein glycoprotein, lipoprotein, and so forth.

In one embodiment of the invention, the cell to be used is transformed or transfected with a nucleic acid molecule which performs a reporter function, such as SEAP, luciferase, green fluorescent protein, and so forth. It is well known that one of ordinary skill in the art can transform or transfect cells with expression vectors which require activation of, e.g., a receptor to cause the promoter to which the reporter molecule is operably linked, to function. Since activation of the receptor molecule depends upon ligand receptor interaction, one can determine the effect of a putative ligand or "anti-ligand" by measuring the reporter molecule function, and comparing it to a control.

Of course, it will be clear to the skilled artisan that it is also possible to measure receptor function directly, as was shown by the examples, supra. There are legions of receptors that are known, as is their effect when linked to a ligand molecule. Determination of one or more of these functions can be used as a determination of the effect of a substance of interest.

The substance of interest may be tested directly, or it may be tested in a competitive assay, using a known antagonist or agonist of a receptor or other molecule of interest. For example, an antibody can be tested for its efficacy as an antagonist of a molecule by mixing it with a known ligand for the molecule, and comparing a property of the target molecule with and without the presence of the antibody. The converse of this type of assay can also be carried out, where the antibody function is known, and the molecule of interest is not an antibody, or is in fact a second antibody.

The features of this invention also afford the user a kit useful in screening for a substance of interest. Such kits may contain, e.g., a separate portion of each of (i) a substance which causes arrested division of a cell, and a substance known to interact with a target molecule of interest. The kit may also include cells transformed or transfected with the molecule of interest, or cells to be transformed or transfected and the agent used for transformation/transfection (e.g., an expression vector), or cells naturally expressing the target molecule of interest or other items. All of the variations set forth supra can be used in these kits. In cases where an additional function of the cells is to be described, that material can be included in the kit as well.

Other features of the invention will be clear to the skilled artisan, and need not be reiterated here.

What is claimed is:

1. A method for determining if a substance of interest has an effect on a G-protein coupled receptor (GPCR) signal in a division arrested mammalian cell, the method comprising:

(a) measuring the signal in the division arrested mammalian cell after the cell is contacted with the substance of interest and comparing the signal with a signal measured when the cell has not been contacted with the substance of interest, and (b) determining whether the substance of interest has an effect on the GPCR signal in the division arrested mammalian cell by identifying a comparative difference in the signal when the division arrested mammalian cell has and has not been contacted with the substance of interest, wherein the division arrested mammalian cell is a mammalian cell in which the meiotic or mitotic cycle has been stopped and in which cellular division can no longer take place.

2. The method of claim 1, wherein activation of the G-protein coupled receptor is measured.

3. The method of claim 1, wherein the G-protein coupled receptor is overexpressed by the division arrested mammalian cell.

4. The method of claim 1, wherein the G-protein coupled receptor is selected from the group consisting of:
   (a) a serotonin receptor;
   (b) a muscaranic acetylcholine receptor; and
   (c) a β2 adrenergic receptor.

5. The method of claim 1, wherein the GPCR signal measured in the division arrested mammalian cell results from $Ca^{2+}$ mobilization.

6. The method of claim 1, wherein the GPCR signal measured in the division arrested mammalian cell is determined by measuring the activity of a reporter.

7. The method of claim 6, wherein the reporter is selected from the group consisting of secreted alkaline phosphatase, luciferase, and green fluorescent protein.

8. The method of claim 1, wherein the division arrested mammalian cell is a cell selected from the group consisting of:
   (a) a Chinese hamster ovary cell;
   (b) a NIH3T3 cell;
   (c) a HEK293 cell; and
   (d) a M1WT3 cell.

9. The method of claim 8, wherein the cell is a Chinese hamster ovary cell.

10. The method of claim 1, wherein the meiotic or mitotic cycle of the mammalian cell has been stopped by irradiation of the mammalian cell or exposure of the mammalian cell to mitomycin C.

11. The method of claim 10, wherein the irradiation of the mammalian cell is gamma irradiation.

12. The method of claim 1, wherein the substance of interest has efficacy as a GPCR agonist.

13. The method of claim 1, wherein the substance of interest has efficacy as a GPCR antagonist.

14. The method of claim 1, wherein the division arrested mammalian cell has been frozen and thawed before contact with the substance of interest.

15. The method of claim 14, wherein the cell is a Chinese hamster ovary cell.

16. The method of claim 1, wherein the division arrested mammalian cell has previously been gamma irradiated.

* * * * *